United States Patent [19]
Waldman

[11] Patent Number: 5,447,527
[45] Date of Patent: Sep. 5, 1995

[54] THERAPEUTIC LIGHT METHOD

[75] Inventor: Murray M. Waldman, Winnipeg, Canada

[73] Assignee: Suzanne Maureen Waldman, Winnipeg, Canada

[21] Appl. No.: 75,674

[22] Filed: Jun. 11, 1993

Related U.S. Application Data

[62] Division of Ser. No. 818,727, Jan. 6, 1992, abandoned.

[30] Foreign Application Priority Data

Apr. 27, 1989 [CA] Canada .................................... 597948

[51] Int. Cl.$^6$ ............................................. A61N 5/06
[52] U.S. Cl. ...................................................... 607/88
[58] Field of Search .................. 600/26; 128/395–398; 607/88–95

[56] References Cited

U.S. PATENT DOCUMENTS 4,858,609 8/1989 Cole ...................................... 600/26

OTHER PUBLICATIONS

Wirz–Justice, *Light Treatment of Seasonal Affective Disorder in Switzerland*, Acta Psychiatr. Scand. 1986:74:193–204.

*Primary Examiner*—Mark S. Graham
*Attorney, Agent, or Firm*—Pascal & Associates

[57] ABSTRACT

A therapeutic method of using a lamp comprised of a fixture for retaining a light bulb in a position to be viewed by the eyes of a patient, apparatus for restricting the wavelengths of light emitted by the light bulb to those between 490 and 520 nanometers, and apparatus for restricting the light energy irradiance to between about 1.8 and 200 microwatts per square centimeter over at least the eyes of the patient. The restricting apparatus can be a narrowband light transmission filter or the phosphor of a fluorescent bulb. By the use of this lamp, the effects of seasonal affective disorder (SAD) or other chronobiological disorders are reduced or eliminated without substantially encountering the side effects of hypomania, irritability, nausea or agitation previously found.

5 Claims, 2 Drawing Sheets

THERAPEUTIC LIGHT METHOD

This application is a division of prior application Ser. No. 07/818,727, filed Jan. 6, 1992, abandoned.

FIELD OF THE INVENTION

This invention relates to a therapeutic lamp which can be used to reduce and/or eliminate the effects of seasonal affective disorder (SAD) or other chronobiological disorders.

1. Background of the Invention

It has been recently discovered that some people in high and low latitude regions of the world suffer from a disorder referred to as seasonal affective disorder (SAD). The symptoms have been shown to be consistent: from mild to clinical depression, aversion to physical and social activity. irregularity of sleeping patterns and craving of carbohydrates (through apparent interference in the production of serotonin, a hormone which affects the recognition that adequate carbohydrates have been ingested).

Indications have pointed to the existence of SAD as being related in some way to a disorder of the circadian rhythm which occurs in many people when daylight hours diminish throughout the winter. The level of melatonin rises in the evening hours and is at a high level throughout the night, reducing in the morning. Persons with SAD appear to have a disturbed melatonin rhythm. It is known that the night time level of melatonin is five times the day time level.

2. Description of the Prior Art

It was recently discovered that the incidence of SAD can be substantially reduced or eliminated by exposing a person to high intensity broad spectrum light. A description of SAD and the light therapy may be found in the SCIENTIFIC AMERICAN January 1989 article entitled "Carbohydrates and Despression" by Richard J. Wurtman and Judith J. Wurtman, pp. 68-75. In this article it is noted that patients who are exposed in the morning to be between 45 and 60 minutes of high intensity broad spectrum light improve after only two or three days of treatment.

Other research on the phenomenon is described in the article "Effect of Light Wavelength on the Suppression of Nocturnal Plasma Melatonin in Normal Volunteers", by G. C. Brainard et al in the annals of The New York Academy of Sciences, Vol. 453, "The Medical and Biological Effects of Light", edited by R. J. Wurtman et al, published by The New York Academy of Sciences, N. Y., N. Y., pp. 376ff, and in the article "Light Treatment of Seasonal Depression" by A. Wirz-Justice et al, pp. 193-204 published in ACTA Psychiatr. Scand, 1986, Vol. 74. In the article by Brainard et al it was established that the efficiency of depression of the melatonin level is highest with light having wavelength centered at about 509 nanometers. In the latter publication it was reported that a side effect in the use of white light gave hypomanic activation, irritability, headache and nausea, while yellow light gave headache, nausea, agitation and irritability and worsening of depression.

SUMMARY OF THE INVENTION

I have determined that it is not necessary to provide a highly intense light as is suggested in the SCIENTIFIC AMERICAN article to provide the therapeutic beneficial result. Rather, in accordance with the present invention, the light energy is restricted to the wavelength of between about 490 and 520 nanometers, and at a substantially reduced total energy irradiance over at least the eyes of the patient, to between about 1.8 and 100 microwatts per square centimeter. The total energy is thus substantially less than that proposed in the prior art. As a result the hypomanic activation, irritability, headache and nausea, and other discomfort caused by the intensity of the light can be substantially reduced or eliminated.

A preferred embodiment of the present invention is a therapeutic lamp comprised of a fixture for retaining a light bulb in a position to be directly viewed by the eyes of a patient, apparatus for restricting the wavelength of the light emitted by the light bulb to between about 490 and 520 nanometers, and apparatus for restricting the light energy irradiance to between about 1.8 and 200 microwatts per square centimeter over at least the eyes of the patient.

The wavelength and energy restriction can be provided by either the light bulb emission itself, or by using a broader spectrum light bulb and a filter disposed adjacent the light bulb so as to shadow at least the eyes of the patient. The light intensity could be obtained by reflection from a surface but the spectrum noted above and the irradiance of the eyes should be maintained.

The light bulb can be retained by and in front of a reflector, the open side of the reflector being closed by the filter.

Therefore the term "restriction" used herein as related to wavelength and/or energy is intended to mean, and should be construed to mean, generation or emission from a source that provides a restricted wavelength and/or intensity, or generation of wider bandwidth energy and/or higher intensity energy and filtering it to the desired wavelength bandwidth and/or reduced energy intensity, or any other means for achieving the desired bandwidth and/or intensity.

BRIEF INTRODUCTION TO THE DRAWINGS

A better understanding of the invention will be obtained by reference to the detailed description below, with reference to the following drawing in which:

FIG. 1 is a side sectional view of the therapeutic lamp in accordance with an embodiment of the present invention, FIG. 2 is a front perspective of the invention showing the light bulb used therein in phantom, FIG. 3 is a transmission graph of a filter used in a successful embodiment of the invention, and FIG. 4 is the energy output spectrum of a fluorescent bulb that can be used in the present invention.

DESCRIPTION OF THE PREFERRED EMBODIMENT

Shown generally at 1 is a person receiving light therapy in order to alleviate the symptoms of SAD. In accordance with the prior art, an intense broad spectrum light is viewed by the patient for several hours per day over several days. This had been shown to substantially reduce the level of melatonin during daylight hours and to maintain its rhythmic variation in synchronization of day and night, substantially alleviating the symptoms.

It has been shown that exposure to the very intense light for several hours a day is very uncomfortable, and can sometimes cause hypomanic activation, irritability, headache and nausea.

Figure 1:
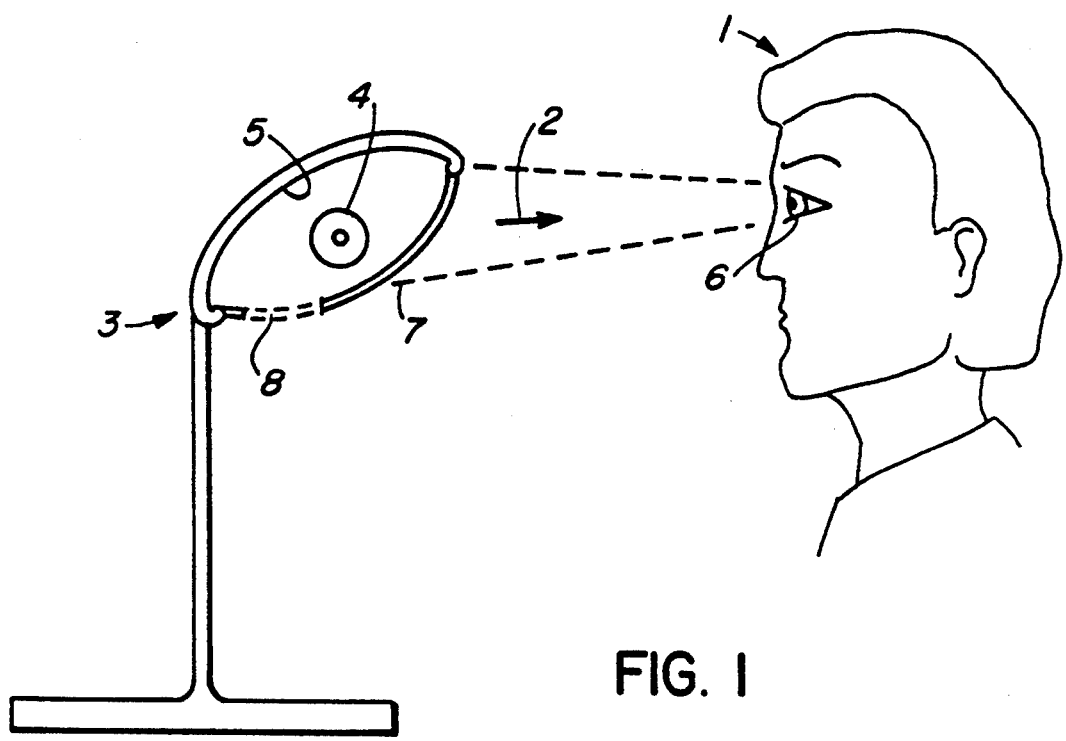
Figure 2:
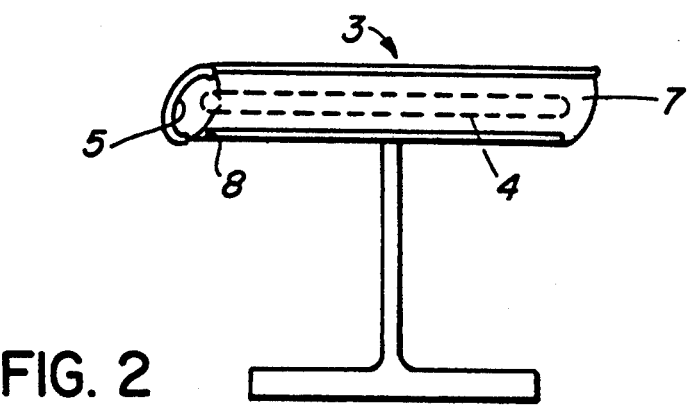

In accordance with the present invention, however, a light which severely restricts the spectrum and the total energy entering the eyes is provided. Shown in FIG. 1 is light (designated by the arrow 2) having wavelength of between 490 and 520 nanometers, and having light energy irradiance of between 1.8 and about 200 microwatts per square centimeter over at least the eyes of the patient 1. This has been found to substantially decrease the discomfort and side effects encountered by the patient 1.

The therapeutic lamp in accordance with an embodiment of the invention is comprised of a fixture 3 for retaining a light bulb 4 in a well known manner, in a position to be directed viewed by the eyes of a patient. The light bulb can be a broad spectrum bulb which is retained in front of a reflector 5 for increasing the efficiency of light transmission in the direction of the eyes 6 of the patient 1.

The front of the fixture is closed by a filter 7 which performs the function of restricting the wavelength of the energy irradiance to between about 490 and 520 nanometers and the energy emission to between about 1.8 and 200 microwatts per square centimeter over at least the eyes of the patient.

The lower light energy irradiance level is the approximate minimum which is found to alleviate SAD symptoms, while the higher figure has been found to be tolerable to avoid irritation of the eye and to bring on the other symptoms noted above. However it will be recognized that different patients have different sensitivity of response to the light, and the limits noted could be somewhat variable for different sensitivities and responses of different patients.

It should be noted that the filter 7 can be gapped over a bottom portion (e.g. there can be a clear portion of the filter or a cutout to the filter) to allow full spectrum light to be emitted downwardly, and not over the eye region of the patient. This will allow full spectrum light to illuminate reading material that the patient may wish to use while using the therapeutic lamp. This gapped region is shown at reference numeral 8. Alternatively the gapped region shown can be covered by a filter providing transmissive qualities in the desired wavelength range, but with higher light transmission than the portion of the light viewed directly. This will allow reflected light of the proper wavelength to reach the eye, e.g. reflected from reading material. Scattering and other losses for this light reduces the irradiance reaching the eye, to provide the desired total irradiance at the eye.

In accordance with another embodiment of the invention, the light bulb itself is of a type which restricts its output to between 490 and 520 nanometers. Depending on the intensity of emission, a filter 7 may be included to restrict the light intensity over at least the eye region of the patient to between about 1.8 and 200 microwatts per square centimeter. If the light bulb itself emits in the correct wavelength range and intensity range, the filter may be dispensed with.

Figure 3:
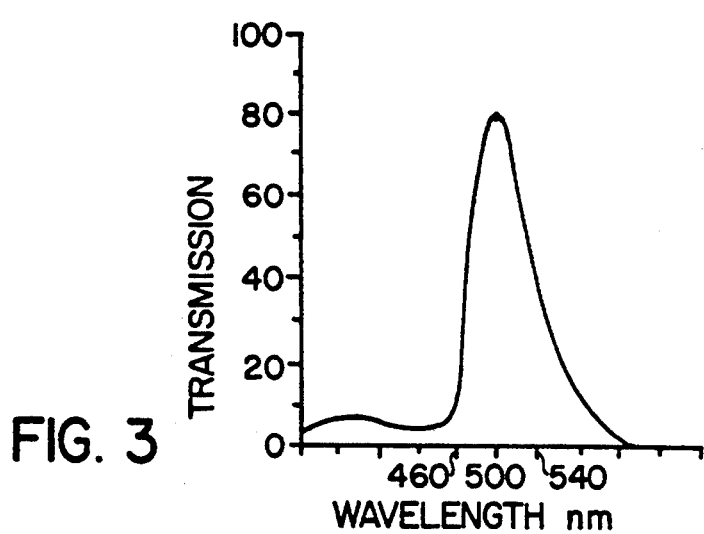

In case a broad spectrum bulb is used, a ROSCOLUX ™ type Chroma Green #75 filter can be used as filter 7, which has a narrow transmission passband restricting the wavelength of emitted light to usable wavelengths. A spectral graph of this filter is shown in FIG. 3. Several thicknesses of filter can be used in order to restrict the light irradiance to between about 1.8 and 200 microwatts per square centimeter over at least the eyes of the patient. The filter is available from Rosco of Markham, Ontario, Canada.

A light bulb which has peak energy at about 530 nanometers, which can be used, is a turquoise lamp manufactured by Duro Test. While the wave spectral energy decreases substantially below about 450 nanometers and above about 620 nanometers, a lamp such as this in combination with the aforenoted ROSCOLUX ™ filter should be used in accordance with one embodiment of the invention.

Figure 4:
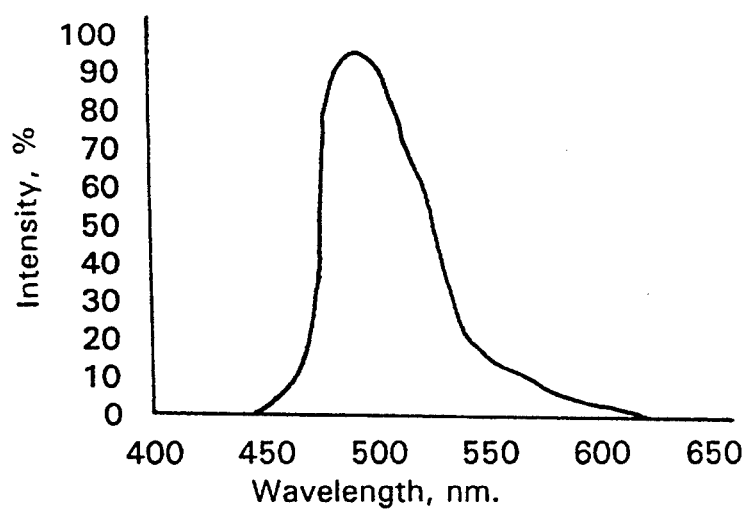

A lamp that emits light within the required wavelength range can be made by fabricating a fluorescent bulb with a gallium magnesium oxide phosphor. The energy output spectrum of such a bulb is shown in FIG. 4.

The light bulb of the lamp is wired and powered in a well known manner, and the reflector that is used should be a standard lamp reflector, although a mirrored reflector will provide highest efficiency. The structure of the lamp, reflector support and other mechanical aspects of the lamp are well known to persons in the lamp manufacturing art and need not be described further.

It may also be desirable for some designs (e.g. with a low intensity bulb) to use a lens in conjunction with the filter in order to concentrate the light to the eye region of the patient. The reflector of the lamp can surround most of the lamp in order to allow emission of the light only over a region of the eyes of the patient and to avoid emission of light downwardly or to regions remote from the eye region of the patient.

A person skilled in the art understanding this invention may now conceive of variations to the above using the principles described herein. All are considered to be within the sphere and scope of the invention as defined in the claims appended hereto.

I claim:

1. A method of treating, without substantial side effects of irritability or irritation of the eyes, a person having chronobiological disorder comprising irradiating the eyes of the person with light energy having wavelengths between about 490 and 520 nanometers and irradiance of between about 1.8 and 200 microwatts per square centimeter for a substantially permanently effective period of at least approximately ¾ hour, in isolation of other stimulants causing recurrence of said disorder.

2. A method as defined in claim 1 in which the irradiating step is conducted by illuminating a broad spectrum light bulb, and filtering the light from said bulb before it reaches the eyes of the person, to said wavelengths.

3. A method as defined in claim 1 in which the wavelengths do not change during the period of the treatment.

4. A method as defined in claim 1, in which the irradiating step is conducted using a lamp comprised of a fixture for retaining a light bulb in a position to be viewed by the eyes of a patient, a light bulb retained in the fixture, means for restricting the wavelengths of light emitted by the light bulb to between about 490 and 520 nanometers and means for restricting the light energy irradiance to between 1.8 and 200 microwatts per square centimeter over at least the eyes of the patient.

5. A method as defined in claim 1, in which the irradiating step is conducted using a lamp comprised of a fixture for retaining a light bulb in a position to be viewed by the eyes of a patient, and a light bulb retained in the fixture, the light bulb comprising means for emitting light having a majority of its energy output restricted to wavelengths between about 490 and 520 nanometers and for providing light energy irradiance of between about 1.8 and 200 microwatts per square centimeter over the eyes the patient.

* * * * *